(12) United States Patent
Lee et al.

(10) Patent No.: US 9,115,362 B2
(45) Date of Patent: Aug. 25, 2015

(54) MUTANT MICROORGANISM HAVING HIGH PRODUCTION OF CADAVERINE, AND PREPARATION METHOD OF CADAVERINE USING SAME

(75) Inventors: Sang Yup Lee, Daejeon (KR); Zhi Gang Qian, Daejeon (KR); Xiaoxia Xia, Daejeon (KR); Min Young Kim, Seoul (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 13/813,949

(22) PCT Filed: Aug. 3, 2011

(86) PCT No.: PCT/KR2011/005709
§ 371 (c)(1),
(2), (4) Date: Mar. 1, 2013

(87) PCT Pub. No.: WO2012/018226
PCT Pub. Date: Feb. 9, 2012

(65) Prior Publication Data
US 2013/0157323 A1    Jun. 20, 2013

(30) Foreign Application Priority Data
Aug. 3, 2010  (KR) .................. 10-2010-0075066

(51) Int. Cl.
| | |
|---|---|
| *C12N 15/70* | (2006.01) |
| *C12N 9/02* | (2006.01) |
| *C12N 9/10* | (2006.01) |
| *C12N 9/88* | (2006.01) |
| *C12N 9/00* | (2006.01) |
| *C12P 13/00* | (2006.01) |
| *C12N 15/52* | (2006.01) |

(52) U.S. Cl.
CPC ............... *C12N 15/70* (2013.01); *C12N 9/001* (2013.01); *C12N 9/104* (2013.01); *C12N 9/1029* (2013.01); *C12N 9/1085* (2013.01); *C12N 9/1096* (2013.01); *C12N 9/88* (2013.01); *C12N 9/93* (2013.01); *C12N 15/52* (2013.01); *C12P 13/001* (2013.01); *C12Y 103/01026* (2013.01); *C12Y 203/01057* (2013.01); *C12Y 205/01016* (2013.01); *C12Y 206/01082* (2013.01); *C12Y 401/0102* (2013.01); *C12Y 402/01052* (2013.01)

(58) Field of Classification Search
CPC ....... C12P 13/001; C12P 13/08; C12N 15/52; C12N 15/70; C12N 9/104; C12N 15/63; C12N 15/67; C12Y 203/01057; C12Y 205/01016; C12Y 206/01082; C12Y 401/0102; C12Y 1/15; C12R 1/15
See application file for complete search history.

(56) References Cited

U.S. PATENT DOCUMENTS

2012/0295317 A1 * 11/2012 Schroder et al. .............. 435/128

FOREIGN PATENT DOCUMENTS

| KR | 10-2009-0005099 A | 1/2009 |
|---|---|---|
| WO | 2007113127 A1 | 10/2007 |

OTHER PUBLICATIONS

Zhi-Gang Qian—Metabolic Engineering of *Escherichia coli* for the Production of Putrescine: A Four Carbon Diamine. Biotechnology and Bioengineering, vol. 104, No. 4, Nov. 1, 2009.*
Zhi-Gang Qian Metabolic Engineering of *Escherichia coli* for the Production of Cadaverine: A Five Carbon Diamine Biotechnology and Bioengineering, vol. 108, No. 1, Jan. 1, 2011.*
Bowman, W., et al., "Spermidine Biosynthesis: Purification and Properties of Propylamine Transferase From *Escherichia coli*", "The Journal of Biological Chemistry", Apr. 10, 1973, pp. 2480-2486, vol. 248, No. 7.
Datsenko, K., et al, "One-step inactivation of chromosomal genes in *Escherichia coli* K-12 using PCR products", "Proc. Natl. Acad. Sci. USA (PNAS)", Jun. 6, 2000, pp. 6640-6645, vol. 97, No. 12.
Gueldener, U., et al, "A new efficient gene disruption cassette for repeated use in budding yeast", "Nucleic Acids Research", 1996, pp. 2519-2524, vol. 24, No. 13.
Hafner, E., et al., "Mutants of *Escherichia coli* That Do Not Contain 1,4-Diaminobutane (Putrescine) or Spermidine", "The Journal of Biological Chemistry", Dec. 25, 1979, pp. 12419-12426, vol. 254, No. 24.
Haywood, G., et al., "The occurrence, subcellular localization and partial purification of diamine acetyltransferase in the yeast *Candida boidinii* grown on spermidine or putrescine as sole nitrogen source", "Eur. J. Biochem.", 1985, pp. 277-283, vol. 148.
Kim, J., et al., "Development of a markerless gene knock-out system for Mannheimia succiniciproducens using a temperature-sensitive plasmid", "FEMS Microbiol Lett", Nov. 16, 2007, pp. 78-85, vol. 278.

(Continued)

*Primary Examiner* — Kagnew H Gebreyesus
(74) *Attorney, Agent, or Firm* — Hultquist, PLLC; Steven J. Hultquist; Mary B. Grant

(57) ABSTRACT

The present invention relates to a mutant microorganism having a high ability to produce cadaverine, and a method for producing cadaverine using the same. More specifically, the invention relates to a mutant microorganism having a high ability to produce cadaverine wherein a gene involved in the cadaverine degradation or utilization pathway is inactivated or deleted, and to a method for producing cadaverine in high yield by culturing the mutant microorganism under aerobic conditions. The mutant microorganism according to the present invention is useful for producing a high yield of cadaverine which can be widely used in various industrial applications.

12 Claims, 3 Drawing Sheets

(56) References Cited

OTHER PUBLICATIONS

Kind, S., et al., "Systems-wide metabolic pathway engineering in *Corynebacterium glutamicum* for bio-based production of diaminopentane", "Metabolic Engineering", Apr. 8, 2010, pp. 341-351, vol. 12.

Kurihara, S., et al., "A Novel Putrescine Utilization Pathway Involves gamma-Glutamylated Intermediates of *Escherichia coli* K-12", "The Journal of Biological Chemistry", Feb. 11, 2005, pp. 4602-4608, vol. 280, No. 6.

Kurihara, S., et al., "gamma-Glutamylputrescine Synthetase in the Putrescine Utilization Pathway of *Escherichia coli* K-12", "The Journal of Biological Chemistry", May 21, 2008, pp. 19981-19990, vol. 283, No. 29.

Mimitsuka, T., et al., "Metabolic Engineering of *Corynebacterium glutamicum* for Cadaverine Fermentation", "Biosci. Biotechnol. Biochem.", Sep. 23, 2007, pp. 2130-2135, vol. 71, No. 9.

Palmeros, B., et al., "A family of removable cassettes designed to obtain antibiotic-resistance-free genomic modifications of *Escherichia coli* and other bacteria", "Gene", 2000, pp. 255-264, vol. 247.

Qian, Z. et al., "Metabolic Engineering of *Escherichia coli* for the Production of Putrescine: A Four Carbon Diamine", "Biotechnol. Bioeng.", Aug. 27, 2009, pp. 651-662, vol. 104, No. 4.

Qian, Z., et al., "Metabolic engineering of *Escherichia coli* for the production of cadaverine: A five carbon diamine", "Biotechnology and Bioengineering", Sep. 30, 2010, pp. 93-103, vol. 108, No. 1.

Sambrook, J., et al., "Molecular Cloning: A Laboratory Manual Third Edition", 2000, Publisher: Cold Spring Harbor Laboratory Press.

Samsonova, N., et al., "Molecular cloning and characterization of *Escherichia coli* K12 ygjG gene", Jan. 31, 2003, pp. 110, vol. 3, No. 2.

Samsonova, N., et al., "Identification of *Escherichia coli* K12 YdcW protein as a gamma-aminobutyraldehyde dehydrogenase", "FEBS Letters", Jul. 5, 2005, pp. 4107-4112, vol. 579.

Soksawatmaekhin, W., et al., "Excretion and uptake of cadaverine by CadB and its physiological functions in *Escherichia coli*", "Molecular Microbiology", 2004, pp. 1401-1412, vol. 51, No. 5.

Tabor, C., et al., "Polyamines in Microorganisms", "Microbiological Reviews", Mar. 1985, pp. 81-99, vol. 49, No. 1.

\* cited by examiner

```
                        SEQUENCE LISTING

<160> NUMBER OF SEQ ID NOS: 27

<210> SEQ ID NO 1
<211> LENGTH: 63
<212> TYPE: DNA
<213> ORGANISM: Artificial
<220> FEATURE:
<223> OTHER INFORMATION: primer 1

<400> SEQUENCE: 1
atataagctt taccgttcgt atagcataca ttatacgaag ttattgccct gaaccgacga      60
ccg                                                                    63

<210> SEQ ID NO 2
<211> LENGTH: 64
<212> TYPE: DNA
<213> ORGANISM: Artificial
```

```
<220> FEATURE:
<223> OTHER INFORMATION: primer 2

<400> SEQUENCE: 2
aattcccggg taccgttcgt ataatgtatg ctatacgaag ttatcatcac ccgacgcact    60
ttgc                                                                64

<210> SEQ ID NO 3
<211> LENGTH: 73
<212> TYPE: DNA
<213> ORGANISM: Artificial
<220> FEATURE:
<223> OTHER INFORMATION: primer 3

<400> SEQUENCE: 3
gtgaaaccag taacgttata cgatrtcgca gagtatgccg gtgtctctta gattggcagc    60
attacacgtc ttg                                                      73

<210> SEQ ID NO 4
<211> LENGTH: 70
<212> TYPE: DNA
<213> ORGANISM: Artificial
<220> FEATURE:
<223> OTHER INFORMATION: primer 4

<400> SEQUENCE: 4
tcactgcccg ctttccagtc gggaaacctg tcgtgccagc tgcattaatg cacttaacgg    60
ctgacatggg                                                          70

<210> SEQ ID NO 5
<211> LENGTH: 70
<212> TYPE: DNA
<213> ORGANISM: Artificial
<220> FEATURE:
<223> OTHER INFORMATION: primer 5

<400> SEQUENCE: 5
cgcctgaata atttcggttg agagatggcg taaggcgtcg ttatctgtcg gacactatag    60
aacgcggccg                                                          70

<210> SEQ ID NO 6
<211> LENGTH: 70
<212> TYPE: DNA
<213> ORGANISM: Artificial
<220> FEATURE:
<223> OTHER INFORMATION: primer 6

<400> SEQUENCE: 6
atgttgcgcc ctttttttac gggtgttaac aaaggaggta tcaacccatg ccgcataggc    60
cactagtgga                                                          70

<210> SEQ ID NO 7
<211> LENGTH: 70
<212> TYPE: DNA
<213> ORGANISM: Artificial
<220> FEATURE:
<223> OTHER INFORMATION: primer 7

<400> SEQUENCE: 7
gaatgtaagg acacgttatg ccaagcgccc acagtgttaa gctacgcccg gacactatag    60
aacgcggccg                                                          70
```

```
<210> SEQ ID NO 8
<211> LENGTH: 70
<212> TYPE: DNA
<213> ORGANISM: Artificial
<220> FEATURE:
<223> OTHER INFORMATION: primer 8

<400> SEQUENCE: 8
ctattgtgcg gtcggcttca ggagagtctg acccggtgtt ttgtgctctg ccgcataggc      60
cactagtgga                                                             70

<210> SEQ ID NO 9
<211> LENGTH: 70
<212> TYPE: DNA
<213> ORGANISM: Artificial
<220> FEATURE:
<223> OTHER INFORMATION: primer 9

<400> SEQUENCE: 9
ctgcaatact aaatcggta tcatgtgata cgcgagcctc cggagcatat gacactatag       60
aacgcggccg                                                             70

<210> SEQ ID NO 10
<211> LENGTH: 70
<212> TYPE: DNA
<213> ORGANISM: Artificial
<220> FEATURE:
<223> OTHER INFORMATION: primer 10

<400> SEQUENCE: 10
cgtcgtatcg ccatccgatt tgatattacg cttcttcgac acttactcgc ccgcataggc      60
cactagtgga                                                             70

<210> SEQ ID NO 11
<211> LENGTH: 70
<212> TYPE: DNA
<213> ORGANISM: Artificial
<220> FEATURE:
<223> OTHER INFORMATION: primer 11

<400> SEQUENCE: 11
gatgaaacaa ccccgcaagg ggtattacgc gttttttcaac atccactcaa gacactatag     60
aacgcggccg                                                             70

<210> SEQ ID NO 12
<211> LENGTH: 70
<212> TYPE: DNA
<213> ORGANISM: Artificial
<220> FEATURE:
<223> OTHER INFORMATION: primer 12

<400> SEQUENCE: 12
cgagcggaaa acaaaccaaa ggcgaagaat catggaaacc aatatcgttg ccgcataggc      60
cactagtgga                                                             70

<210> SEQ ID NO 13
<211> LENGTH: 70
<212> TYPE: DNA
<213> ORGANISM: Artificial
<220> FEATURE:
<223> OTHER INFORMATION: primer 13

<400> SEQUENCE: 13
```

```
tcaccatcat acaacggcac tttgcgatag cggcggatca gataccataa gacactatag      60
aacgcggccg                                                             70

<210> SEQ ID NO 14
<211> LENGTH: 76
<212> TYPE: DNA
<213> ORGANISM: Artificial
<220> FEATURE:
<223> OTHER INFORMATION: primer 14

<400> SEQUENCE: 14
ggtgagttgt tcttaaggaa agcataaaaa aaacatgcat acaacaatca gaacgggaca      60
ctatagaacg cggccg                                                     76

<210> SEQ ID NO 15
<211> LENGTH: 75
<212> TYPE: DNA
<213> ORGANISM: Artificial
<220> FEATURE:
<223> OTHER INFORMATION: primer 15

<400> SEQUENCE: 15
tatccgctca caattccaca cattatacga gccggatgat taattgtcaa cagctccgca      60
taggccacta gtgga                                                      75

<210> SEQ ID NO 16
<211> LENGTH: 72
<212> TYPE: DNA
<213> ORGANISM: Artificial
<220> FEATURE:
<223> OTHER INFORMATION: primer 16

<400> SEQUENCE: 16
tcaccagata atgttgcgat gacagtgtca aactggttat tcctttaagg ggtgagttgt      60
tcttaaggaa ag                                                         72

<210> SEQ ID NO 17
<211> LENGTH: 76
<212> TYPE: DNA
<213> ORGANISM: Artificial
<220> FEATURE:
<223> OTHER INFORMATION: primer 17

<400> SEQUENCE: 17
gtaacaatcg cgacaatact tcccgtgaac atggtctgtt tcctgtgtga aattgttatc      60
cgctcacaat tccaca                                                     76

<210> SEQ ID NO 18
<211> LENGTH: 73
<212> TYPE: DNA
<213> ORGANISM: Artificial
<220> FEATURE:
<223> OTHER INFORMATION: primer 18

<400> SEQUENCE: 18
taagttaacg gcggccatta gcgctctctc gcaatccggt aatccatatc attgacacta      60
tagaacgcgg ccg                                                        73

<210> SEQ ID NO 19
<211> LENGTH: 71
<212> TYPE: DNA
```

-continued

<213> ORGANISM: Artificial
<220> FEATURE:
<223> OTHER INFORMATION: primer 19

<400> SEQUENCE: 19
ctcagtcagg cttccggcgg tcattaccgc atgaaaaatt tcaatatgac gtaagttaac    60
ggcggccatt a                                                         71

<210> SEQ ID NO 20
<211> LENGTH: 78
<212> TYPE: DNA
<213> ORGANISM: Artificial
<220> FEATURE:
<223> OTHER INFORMATION: primer 20

<400> SEQUENCE: 20
gatcggtatc ggtgctgaac agtgaatgtg gcatggtctg tttcctgtgt gaaattgtta    60
tccgctcaca attccaca                                                  78

<210> SEQ ID NO 21
<211> LENGTH: 64
<212> TYPE: DNA
<213> ORGANISM: Artificial
<220> FEATURE:
<223> OTHER INFORMATION: primer 21

<400> SEQUENCE: 21
gtcattcatc gactcatgcc tttcactgat atccctccct gtttgacact atagaacgcg    60
gccg                                                                 64

<210> SEQ ID NO 22
<211> LENGTH: 61
<212> TYPE: DNA
<213> ORGANISM: Artificial
<220> FEATURE:
<223> OTHER INFORMATION: primer 22

<400> SEQUENCE: 22
tggctctggc gtcgtaacct gtcacatgtt attggcatgc agtcattcat cgactcatgc    60
c                                                                    61

<210> SEQ ID NO 23
<211> LENGTH: 71
<212> TYPE: DNA
<213> ORGANISM: Artificial
<220> FEATURE:
<223> OTHER INFORMATION: primer 23

<400> SEQUENCE: 23
ggcaacgcgg atgtttgcat catgcatggt ctgtttcctg tgtgaaattg ttatccgctc    60
acaattccac a                                                         71

<210> SEQ ID NO 24
<211> LENGTH: 57
<212> TYPE: DNA
<213> ORGANISM: Artificial
<220> FEATURE:
<223> OTHER INFORMATION: primer 24

<400> SEQUENCE: 24
gatgtgaaag gcttccagca gtgggtggct gaggtgctgg ctctggcgtc gtaacct       57

```
<210> SEQ ID NO 25
<211> LENGTH: 61
<212> TYPE: DNA
<213> ORGANISM: Artificial
<220> FEATURE:
<223> OTHER INFORMATION: primer 25

<400> SEQUENCE: 25
tgaatcaact ggcggcccat acgcccccg gctcccgcga tggcaacgcg gatgtttgca    60
t                                                                  61

<210> SEQ ID NO 26
<211> LENGTH: 31
<212> TYPE: DNA
<213> ORGANISM: Artificial
<220> FEATURE:
<223> OTHER INFORMATION: primer 26

<400> SEQUENCE: 26
cgtcgaattc atgaacgtta ttgcaatatt g                                 31

<210> SEQ ID NO 27
<211> LENGTH: 32
<212> TYPE: DNA
<213> ORGANISM: Artificial
<220> FEATURE:
<223> OTHER INFORMATION: primer 27

<400> SEQUENCE: 27
gctcgagctc ttattttttg ctttcttctt tc                                32
```

MUTANT MICROORGANISM HAVING HIGH PRODUCTION OF CADAVERINE, AND PREPARATION METHOD OF CADAVERINE USING SAME

CROSS-REFERENCE TO RELATED APPLICATIONS

This application is a U.S. national phase under the provisions of 35 U.S.C. §371 of International Patent Application No. PCT/KR11/05709 filed Aug. 3, 2011, which in turn claims priority of Korean Patent Application No. 10-2010-0075066 filed Aug. 3, 2010. The disclosures of such international patent application and Korean priority patent application are hereby incorporated herein by reference in their respective entireties, for all purposes.

TECHNICAL FIELD

The present invention relates to a mutant microorganism having a high ability to produce cadaverine, and a method for producing cadaverine using the same. More specifically, the invention relates to a mutant microorganism having a high ability to produce cadaverine wherein a gene involved in the cadaverine degradation or utilization pathway is inactivated or deleted, and to a method for producing cadaverine in high yield by culturing the mutant microorganism under aerobic conditions.

BACKGROUND ART

Cadaverine, also known as 1,5-diaminopentane, is an important platform chemical with many industrial applications. Cadaverine serves as the component of polymers such as polyamide or polyurethane, chelating agents, or other additives. In particular, polyamide-5,4 is prepared by polycondensation of cadaverine or succinic acid. Polyamide-5,4 having an annual global market of 3.5 million tons is expected to become a biodiesel alternative to conventional petroleum-based polyamides (Mimitsuka et al., *Biosci. Biotechnol. Biochem.*, 71:2130-2135, 2007; Kind et al., *Met. Eng.*, 12:341-351, 2010). For the production of cadaverine, a renewable, biomass-based carbon source is required.

Cadaverine is a polyamine found in a few microorganisms (Tabor and Tabor, *Microbiol Rev.*, 49:81-99, 1985). In the gram negative bacterium *E. coli*, cadaverine is biosynthesized from L-lysine by L-lysine decarboxylase (see FIG. 1). There are two forms of L-lysine decarboxylase: one is a constitutive one encoded by the ldcC gene, and the other is an inducible one at low pH, which is encoded by the cadA gene. The level of cadaverine in *E. coli* is regulated by biosynthesis, degradation, uptake and export (Soksawatmaekhin et al., *Mol Microbiol.*, 51:1401-1412, 2004).

It was reported that cadaverine is not detectable in wild-type *E. coli* and trace amounts of cadaverine are present in mutants that are defective in the biosynthesis of polyamines (Hafner et al., *J. Biol. Chem.*, 254: 12419-12426, 1979). Although it was reported that a very small amount of cadaverine is present in microorganisms, microorganisms can tolerate a higher concentration of cadaverine. For example, wild-type *Corynebacterium glutamicum* is able to grow in the presence of about 0.3M cadaverine, although it does not biosynthesize cadaverine (Mimitsuka et al., *Biosci. Biotechnol. Biochem.*, 71:2130-2135, 2007). The high tolerance of microorganisms to cadaverine implies that the microorganisms might potentially be metabolically engineered to overproduce cadaverine to industrially useful levels.

European Patent Publication No. 0726240 A1 discloses a method of producing cadaverine by fermentation using inexpensive industrial waste products or materials having protein and a major constituent. However, there is a problem in that, because the disclosed materials are very complex, many purification steps have to be carried out in order to obtain cadaverine and putrescine. WO 2007/113127 A1 discloses a process of biochemically producing cadaverine using recombinant microorganisms. In this patent publication, in order to increase the conversion of lysine to cadaverine, the activity of lysine decarboxylase is increased by overexpressing lysine decarboxylase encoded by the ldcC gene that is involved in this conversion. In this case, the increase in lysine decarboxylase activity results in an increase in the amount of cadaverine, but the degradation of cadaverine is also induced.

Studies on the degradation and utilization of cadaverine in microorganisms are as follows. Bowman et al. have reported that putrescine/cadaverine aminopropyl transferase which is the product of speE promotes the biosynthesis of aminopropyl cadaverine from cadaverine in *E. coli* (Bowman et al., *J. Biol. Chem.*, 248:2480-2486, 1973).

Haywood et al. have reported that the yeast *Candida boidinii* acetylates putrescine to N-acetylputrescine by N-acetyltransferase. It appears that spermidine acetyltransferase which is the *E. coli* speG gene product has high homology with the N-acetyltransferase of the yeast, and thus possess cadaverine acetyltransferase (Haywood and Large, Eur. J. Biochem., 148:277-283, 1985).

Samsonova et al. have reported that another putrescine degradation pathway involves YgjG putrescine/cadaverine aminotransferase and YdcW dehydrogenase without γ-glutamylation (Samsonova et al., *BMC Microbiol.*, 3:2, 2003; Samsonova et al., *FEBS Lett.*, 579:4107-4112, 2005).

Kurihara et al. has called the putrescine degradation pathway as "Puu catabolic pathway" based on the finding that the putrescine degradation pathway is closely associated with γ-glutamylated metabolites of *E. coli*. This pathway appears to be also involved in cadaverine degradation. For example, glutamate-putrescine/glutamate-cadaverine ligase encoded by the puuA gene that is involved in this pathway can covert cadaverine into γ-glutamyl-L-cadaverine. Additionally, a putrescine importer which is the product of the puuP gene is associated with the catabolic pathway and major putrescine importers (Kurihara et al., *J. Biol. Chem.*, 280: 4602-4608, 2005). It can be thought that such putrescine importers introduce cadaverine, because cadaverine is structurally similar to putrescine.

Accordingly, the present inventors have prepared a mutant microorganism wherein at least one gene selected from the group consisting of a speE gene encoding putrescine/cadaverine aminopropyl transferase, a speG gene encoding spermidine N-acetyltransferase, a ygjG gene encoding putrescine/cadaverine aminotransferase, a puuP gene encoding putrescine importer, and a puuA gene encoding glutamate-putrescine/glutamate-cadaverine ligase, which are involved in the cadaverine degradation or utilization pathway of cadaverine-producing microorganisms, is inactivated or deleted, and have found that, when the mutant microorganism is cultured, it can produce cadaverine in high yield, thereby completing the present invention.

DISCLOSURE OF INVENTION

Technical Problem

It is an object of the present invention to provide a mutant microorganism having a high ability to produce cadaverine wherein at least one gene involved in the cadaverine degradation or utilization pathway is inactivated or deleted, and a method for preparing the microorganism.

Another object of the present invention to a method for producing cadaverine in high yield by culturing the microorganism.

Technical Solution

To achieve the above objects, the present invention provides a mutant microorganism having the ability to produce cadaverine wherein at least one gene selected from the group consisting of a speE gene encoding putrescine/cadaverine aminopropyl transferase, a speG gene encoding spermidine N-acetyltransferase, a ygjG gene encoding putrescine/cadaverine aminotransferase, a puuP gene encoding putrescine importer, and a puuA gene encoding glutamate-putrescine/glutamate-cadaverine ligase, which are involved in the cadaverine degradation or utilization pathway, is inactivated or deleted.

The present invention also provides a mutant microorganism having the ability to produce cadaverine wherein at least one gene selected from the group consisting of a speE gene encoding putrescine/cadaverine aminopropyl transferase, a speG gene encoding spermidine N-acetyltransferase, a ygjG gene encoding putrescine/cadaverine aminotransferase, a puuP gene encoding putrescine importer and a puuA gene encoding glutamate-putrescine/glutamate-cadaverine ligase, which are involved in the cadaverine degradation or utilization pathway, is inactivated or deleted, and wherein a native promoter of at least one gene selected from the group consisting of a dapA gene encoding dihydrodipicolinate synthase, a lysA gene encoding diaminopimelate decarboxylase, and a dapB gene encoding dihydrodipicolinate reductase is replaced with a strong promoter.

The present invention also provides a mutant microorganism having the ability to produce cadaverine wherein at least one gene selected from the group consisting of a speE gene encoding putrescine/cadaverine aminopropyl transferase, a speG gene encoding spermidine N-acetyltransferase, a ygjG gene encoding putrescine/cadaverine aminotransferase, a puuP gene encoding putrescine importer, and a puuA gene encoding glutamate-putrescine/glutamate-cadaverine ligase, which are involved in the cadaverine degradation or utilization pathway, is inactivated or deleted, wherein a lacI gene encoding a lac operon repressor is deleted, and also wherein a cadA gene encoding lysine decarboxylase is introduced or amplified.

The present invention also provides a method for preparing a mutant microorganism having the ability to produce cadaverine, the method comprising: inactivating or deleting at least one gene selected from the group consisting of a speE gene encoding putrescine/cadaverine aminopropyl transferase, a speG gene encoding spermidine N-acetyltransferase, a ygjG gene encoding putrescine/cadaverine aminotransferase, a puuP gene encoding putrescine importer, and a puuA gene encoding glutamate-putrescine/glutamate-cadaverine ligase, which are involved in the cadaverine degradation or utilization pathway, from a microorganism having a cadaverine production pathway.

The present invention also provides a method for preparing a mutant microorganism having the ability to produce cadaverine, the method comprising: inactivating or deleting at least one gene selected from the group consisting of a speE gene encoding putrescine/cadaverine aminopropyl transferase, a speG gene encoding spermidine N-acetyltransferase, a ygjG gene encoding putrescine/cadaverine aminotransferase, a puuP gene encoding putrescine importer, and a puuA gene encoding glutamate-putrescine/glutamate-cadaverine ligase, which are involved in the cadaverine degradation or utilization pathway, from a microorganism having a cadaverine production pathway; and replacing a native promoter of at least one gene selected from the group consisting of a dapA gene encoding dihydrodipicolinate synthase, a lysA gene encoding diaminopimelate decarboxylase, and a dapB gene encoding dihydrodipicolinate reductase, which are present in the microorganism having the cadaverine production pathway, with a strong promoter.

The present invention also provides a method for preparing a mutant microorganism having the ability to produce cadaverine, the method comprising: inactivating or deleting at least one gene selected from the group consisting of a speE gene encoding putrescine/cadaverine aminopropyl transferase, a speG gene encoding spermidine N-acetyltransferase, a ygjG gene encoding putrescine/cadaverine aminotransferase, a puuP gene encoding putrescine importer, and a puuA gene encoding glutamate-putrescine/glutamate-cadaverine ligase, which are involved in the cadaverine degradation or utilization pathway, from a microorganism having a cadaverine production pathway; deleting a (lacI) gene encoding a lac operon repressor from the microorganism; and introducing or amplifying a cadA gene encoding lysine decarboxylase in the microorganism.

The present invention also provides a method for producing cadaverine, the method comprising the steps of: culturing the above-described mutant microorganism to produce cadaverine; and recovering cadaverine from the culture.

BEST MODE FOR CARRYING OUT THE INVENTION

As used herein, the term "inactivating" or "inactivated" is meant to comprehend the mutation, substitution (replacement) or deletion of one or more bases of a target gene or the introduction of one or more bases into the gene, so as to reduce the activity of an enzyme which is expressed by the gene, thereby partially or wholly blocking the biosynthetic pathway in which the enzyme is involved.

As used herein, the term "deleting" or "deleted" is meant to comprehend the mutation, substitution (replacement) or deletion of the whole or a part of a target gene or the introduction of one or more bases into the gene, so that the gene is not expressed or does not exhibit enzymatic activity, and further, so that, even though it is expressed, the gene-associated biosynthetic pathway is blocked.

As used herein, the term "amplifying" or "amplified" is meant to comprehend the mutation, substitution (replacement) or deletion of one or more bases of a target gene, the introduction of one or more bases into the gene or the introduction of another microbial gene encoding the same enzyme, so as to increase the activity of the corresponding enzyme.

Figure 1:
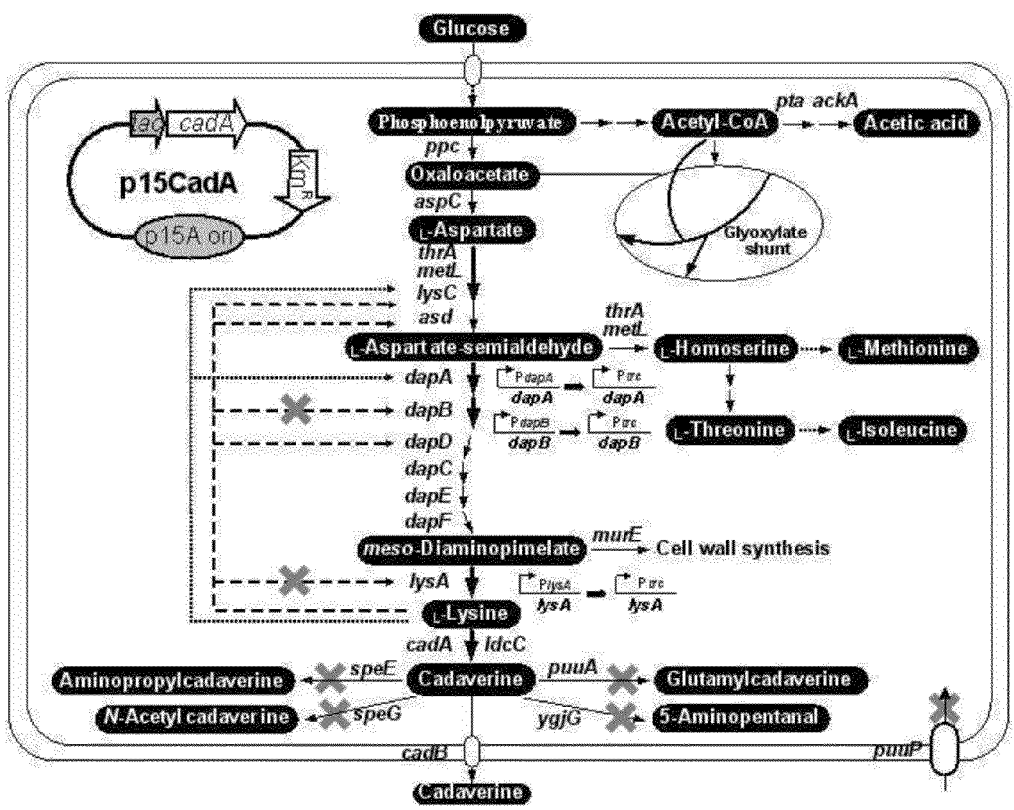
FIG. 1 is a schematic diagram showing a pathway for the synthesis of cadaverine from glucose.

FIG. 1 is a schematic diagram showing a pathway for the synthesis of cadaverine from glucose. As shown in FIG. 1, the present inventors have found that, when gene(s) (speE, speG, ygjG, puuP, and puuA) involved in the cadaverine degradation or utilization pathway of a cadaverine-producing microorganism is inactivated or deleted, cadaverine can be produced in high yield. Reduced activities of the genes (speE, speG, ygjG, puuP, and puuA) involved in the cadaverine degradation or utilization pathway could be confirmed by reduced transcriptional and translational efficiency as compared to those of the respective wild-type genes.

In the Examples of the present invention, the present inventors prepared a mutant microorganism wherein at least one gene selected from the group consisting of a speE gene encoding putrescine/cadaverine aminopropyl transferase, a speG gene encoding spermidine N-acetyltransferase, a ygjG gene encoding putrescine/cadaverine aminotransferase, a puuP gene encoding putrescine importer and a puuA gene encoding glutamate-putrescine/glutamate-cadaverine ligase, which are involved in the cadaverine degradation or utilization pathway, was deleted, and found that the microorganism had an improved ability to produce cadaverine.

Thus, in one aspect, the present invention is directed to a mutant microorganism having the ability to produce cadaverine wherein at least one gene selected from the group consisting of a speE gene encoding putrescine/cadaverine aminopropyl transferase, a speG gene encoding spermidine N-acetyltransferase, a ygjG gene encoding putrescine/cadaverine aminotransferase, a puuP gene encoding putrescine importer, and a puuA gene encoding glutamate-putrescine/glutamate-cadaverine ligase, which are involved in the cadaverine degradation or utilization pathway, is inactivated or deleted, and a method for preparing the same.

In the mutant microorganism of the present invention, a lacI gene encoding a lac operon repressor may further be deleted in order to increase the expression of genes encoding enzymes which are involved in cadaverine biosynthesis. Examples of the genes encoding the enzyme which are involved in cadaverine biosynthesis include dapA, dapB, dapD, dapC, dapE, dapF, lysA and the like.

In the mutant microorganism of the present invention, a cadA gene encoding lysine decarboxylase may further be introduced or amplified.

The cadA gene encoding lysine decarboxylase is introduced in the form of an expression vector containing a strong promoter. The strong promoter may be selected from the group consisting of a trc promoter, a tac promoter, a T7 promoter, a lac promoter, and a trp promoter.

As the microorganism, any microorganism may be used without particular limitation, as long as it produces cadaverine from glucose. Examples of the microorganism include *Bacillus* sp., *Corynebacterium* sp., *Escherichia* sp., *Pichia* sp., *Pseudomonas* sp., *Saccharomyces* sp., etc.

In the present invention, it was also found that, in a mutant microorganism wherein the gene(s) involved in the cadaverine or utilization pathway is deleted, when the native promoter of at least one gene selected from the group consisting of a dapA encoding dihydrodipicolinate synthase, a lysA gene encoding diaminopimelate decarboxylase and a dapB gene encoding dihydrodipicolinate reductase is replaced with a strong promoter, the resulting microorganism can produced in a higher yield.

In Examples of the present invention, based on a mutant microorganism wherein the gene(s) (speE, speG, ygjG, puuP, and puuA) involved in the cadaverine degradation and utilization pathway and the lacI gene encoding the lac operon repressor were deleted, the present inventors prepared the following microorganisms: a mutant microorganism (XQ56) wherein the promoter of the dapA gene encoding dihydrodipicolinate synthase was replaced with the strong promoter trc; a mutant microorganism (XQ59) wherein the promoter of the diaminopimelate decarboxylase-encoding lysA gene of the microorganism XQ56 was replaced with the strong promoter trc; and a mutant microorganism (XQ60) wherein the promoter of the dihydrodipicolinate reductase-encoding dapB gene of the microorganism XQ59 was replaced with the strong promoter trc. Also, a p15CadA vector was introduced into these mutant microorganisms to produce XQ56/p15CadA, XQ59/p15CadA, and XQ60/p15CadA, after which the mutant microorganisms were cultured and found to have a significantly increased ability to produce cadaverine.

Thus, in another aspect, the present invention is directed to a mutant microorganism having the ability to produce cadaverine wherein at least one gene selected from the group consisting of a speE gene encoding putrescine/cadaverine aminopropyl transferase, a speG gene encoding spermidine N-acetyltransferase, a ygjG gene encoding putrescine/cadaverine aminotransferase, a puuP gene encoding putrescine importer and a puuA gene encoding glutamate-putrescine/glutamate-cadaverine ligase, which are involved in the cadaverine degradation or utilization pathway, is inactivated or deleted, and wherein a native promoter of at least one gene selected from the group consisting of a dapA gene encoding dihydrodipicolinate synthase, a lysA gene encoding diaminopimelate decarboxylase, and a dapB gene encoding dihydrodipicolinate reductase is replaced with a strong promoter, and a method for preparing the same.

The promoter of the dapA gene encoding dihydrodipicolinate synthase is suppressed by intracellular DAP or its precursor (L,L-diaminopimelate). Thus, when the promoter of the dapA gene is replaced with a strong promoter, the metabolic flux to lysine can be increased. Also, the promoter of the lysA gene encoding diaminopimelate decarboxylase is suppressed by lysine, and thus when the promoter of the lysA gene with a strong promoter, the metabolic flux to cadaverine can be increased. In addition, the promoter of the dapB gene encoding dihydrodipicolinate reductase is suppressed by lysine, and thus when the promoter of the dapB gene is replaced with a strong promoter, the metabolic flux to cadaverine can be increased.

As described above, in the mutant microorganism of the present invention, the lacI gene encoding the lac operon repressor can further be deleted in order to increase the expression of genes encoding enzymes involved in cadaverine biosynthesis, and the gene cadA gene encoding lysine decarboxylase may further be introduced or amplified.

The cadA gene encoding lysine decarboxylase may be introduced in the form of an expression vector containing a strong promoter. The strong promoter may be selected from the group consisting of a trc promoter, a tac promoter, a T7 promoter, a lac promoter, and a trp promoter.

In still another aspect, the present invention is directed to a method for producing cadaverine, the method comprising the steps of: culturing the above-described mutant microorganism to produce cadaverine; and recovering cadaverine from the culture.

In the present invention, the culture of the mutant microorganism and the recovery of cadaverine from the culture broth can be carried out using a culture method (batch culture or fed-batch culture) known in conventional fermentation processes, and cadaverine separation and purification methods known in the art.

In the present invention, the biosynthetic production of cadaverine can be carried out in vivo or in vitro.

EXAMPLES

Hereinafter, the present invention will be described in further detail with reference to examples. It will be obvious to a person having ordinary skill in the art that these examples are illustrative purposes only and are not to be construed to limit the scope of the present invention.

Particularly, although only specific kinds of vectors for removing target genes and the cadaverine-producing microorganisms of *Escherichia* sp. serving as host cells were illustrated in the following examples, it will also be obvious to a person skilled in the art to use other types of vectors and cadaverine-producing microorganisms.

Example 1

Preparation of Mutant Microorganisms Wherein Gene(s) Involved in the Cadaverine Degradation or Utilization Pathway is Deleted In the present invention, the deletion of gene(s) (speE, speG, ygjG, puuA, and puuP) on the chromosomes was performed by double-crossover homologous recombination (Datsenko, K. A., & Wanner, B. L. *Proc. Natl. Acad. Sci.*, 97:6640-6645, 2000). A lox71-chloramphenicol marker (Cm$^R$)-lox66 cassette was prepared by PCR using primers containing 50 nucleotides homologous to the upstream and downstream regions of the target gene. pECmulox (Kim, J. M., Lee, K. H. & Lee, S. Y., *FEMS Microbiol. Lett.*, 278: 78-85, 2008) containing the lox71-Cm$^R$-lox66 cassette was used as a template in PCR.

The PCR products were transformed into electrocompetent *E. coli* cells containing λ recombinase. Colonies were selected on Luria-Bertani (LB) agar (Sambrook, J., Fritsch E. F., & Maniatis, T., Molecular cloning: a laboratory manual, 3rd edition, Cold Spring Harbor Laboratory Press, 2000) media containing 34 µg/ml of chloramphenicol (Cm). Successful gene replacement with Cm$^R$ was confirmed by direct colony PCR. The antibiotic marker was eliminated by a helper plasmid pJW168 (Lucigen Corporation, Middleton, Wis., USA) containing a temperature-sensitive replication origin and expressing the IPTG-inducible cre recombinase (Palmeros et al., *Gene*, 247:255-264, 2000).

For reference, pECmulox was prepared by performing PCR using the plasmid pACYC184 (New England Biolabs, Ipswich, Mass., USA) as a template and primers of SEQ ID NOS: 1 and 2, digesting the PCR product with HindIII and SmaI restriction enzymes, and ligating the digested product with a pUG6 (Guldener, U et al. *Nucleic Acids Res.*, 24:2519~2524, 1996) plasmid digested with the same restriction enzymes.

[SEQ ID NO: 1]:
5'-ATATAAGCTTTACCGTTCGTATAGCATACATTATACGAAGTTATT

GCCCTGAACCGACGACCG-3'

[SEQ ID NO: 2]:
5'-AATTCCCGGGTACCGTTCGTATAATGTATGCTATACGAAGTTATC

ATCACCCGACGCACTTTGC-3'

1-1: Preparation of WL3110 Strain

PCR was performed using the plasmid pECmulox as a template and primers of SEQ ID NOS: 3 and 4 to obtain a PCR product in which the lacI gene was deleted. The PCR product was then purified and electroporated into electrocompetent *E. coli* (W3110) containing λ recombinase, to thereby produce a WL3110 strain (W3110 Δ lacI).

[SEQ ID NO: 3]:
5'GTGAAACCAGTAACGTTATACGATRTCGCAGAGTATGCCGGTGTC

TCTTAGATTGGCAGCATTACACGTCTTG-3'

[SEQ ID NO: 4]:
5'-TCACTGCCCGCTTTCCAGTCGGGAAACCTGTCGTGCCAGCTGCA

TTAATGCACTTAACGGCTGACATGGG-3'

1-2: Preparation of XQ08 Strain

PCR was performed using the plasmid pECmulox as a template and primers of SEQ ID NOS: 5 and 6 to obtain a PCR product in which the speE gene was deleted. The PCR product was then purified and electroporated into the WL3110 strain prepared in Example 1-1 to thereby produce a XQ08 strain (W3110 ΔlacIΔspeE).

[SEQ ID NO: 5]:
5'-CGCCTGAATAATTTCGGTTGAGAGATGGCGTAAGGCGTCGTTATC

TGTCGGACACTATAGAACGCGGCCG-3'

[SEQ ID NO: 6]:
5'-ATGTTGCGCCCTTTTTTTACGGGTGTTAACAAAGGAGGTATCAAC

CCATGCCGCATAGGCCACTAGTGGA-3'

1-3: Preparation of XQ11 Strain

PCR was performed using the plasmid pECmulox as a template and primers of SEQ ID NOS: 7 and 8 to obtain a PCR product in which the speE gene was deleted. The PCR product was then purified and electroporated into the XQ08 strain prepared in Example 1-2 to thereby produce a XQ11 strain (W3110 ΔlacI ΔspeE ΔspeG).

[SEQ ID NO: 7]:
5'-GAATGTAAGGACACGTTATGCCAAGCGCCCACAGTGTTAAGCTA

CGCCCGGACACTATAGAACGCGGCCG-3'

[SEQ ID NO: 8]:
5'-CTATTGTGCGGTCGGCTTCAGGAGAGTCTGACCCGGTGTTTTGT

GCTCTGCCGCATAGGCCACTAGTGGA-3'

1-4: Preparation of XQ21 Strain

PCR was performed using the plasmid pECmulox as a template and primers of SEQ ID NOS: 9 and 10 to obtain a PCR product in which the speE gene was deleted. The PCR product was then purified and electroporated into the XQ11 strain prepared in Example 1-3 to thereby produce a XQ21 strain (W3110 ΔlacI ΔspeE ΔspeG ΔygjG).

[SEQ ID NO: 9]:
5'-CTGCAATACTTAAATCGGTATCATGTGATACGCGAGCCTCCGGA

GCATATGACACTATAGAACGCGGCCG-3'

[SEQ ID NO: 10]:
5'-CGTCGTATCGCCATCCGATTTGATATTACGCTTCTTCGACACTT

ACTCGCCCGCATAGGCCACTAGTGGA-3'

1-5 Preparation of XQ27 Strain

PCR was performed using the plasmid pECmulox as a template and primers of SEQ ID NOS: 11 and 12 to obtain a PCR product in which the puuA gene was deleted. Meanwhile, PCR was performed using the plasmid pECmulox as a template and primers of SEQ ID NOS: 12 and 13 to obtain a PCR product in which the puuP gene was deleted. The PCR products were then purified and sequentially electroporated into the XQ21 strain prepared in Example 1-4 to thereby produce a XQ27 strain (W3110 ΔlacI ΔspeE ΔspeG ΔygjG ΔpuuP ΔpuuA).

[SEQ ID NO: 11]:
5'-GATGAAACAACCCCGCAAGGGGTATTACGCGTTTTTCAACATCCA

CTCAAGACACTATAGAACGCGGCCG-3'

[SEQ ID NO: 12]:
5'-CGAGCGGAAAACAAACCAAAGGCGAAGAATCATGGAAACCAATAT

CGTTGCCGCATAGGCCACTAGTGGA-3'

[SEQ ID NO: 13]:
5'-TCACCATCATACAACGGCACTTTGCGATAGCGGCGGATCAGATAC

CATAAGACACTATAGAACGCGGCCG-3'

Example 2

Replacement of Promoter

In order to improve the ability to produce cadaverine, the promoter of the mutant strain XQ27 prepared in Example 1-5 was replaced with a strong promoter (trc).

2-1: Preparation of XQ56 Strain

Replacement of the native promoter of the dihydrodipicolinate synthase-encoding dapA gene operon with the trc promoter was carried out in the following manner.

A DNA fragment of fused lox71-chloramphenicol antibiotic marker-lox66 was produced by first PCR reaction using pECmulox as a template and primers of SEQ ID NOS: 14 and 15.

[SEQ ID NO: 14]:
5'-GGTGAGTTGTTCTTAAGGAAAGCATAAAAAAACATGCATACAAC

AATCAGAACGGGACACTATAGAACGCGGCCG-3'

[SEQ ID NO: 15]:
5'-TATCCGCTCACAATTCCACACATTATACGAGCCGGATGATTAATT

GTCAACAGCTCCGCATAGGCCACTAGTGGA-3'

In order to introduce the trc promoter, second PCR reaction was performed using the first PCR product as a template and primers of SEQ ID NOS: 16 and 17.

[SEQ ID NO: 16]:
5'-TCACCAGATAATGTTGCGATGACAGTGTCAAACTGGTTATTCCTT

TAAGGGGTGAGTTGTTCTTAAGGAAAG-3'

[SEQ ID NO: 17]:
5'-GTAACAATCGCGACAATACTTCCCGTGAACATGGTCTGTTTCCTG

TGTGAAATTGTTATCCGCTCACAATTCCACA-3'

The final PCR product was electroporated into the XQ27 strain (W3110 ΔlacI ΔspeE ΔspeG ΔygjG ΔpuuP ΔpuuA). The resultant cells of the mutant microorganism were cultured on an agar medium containing chloramphenicol while only cells in which double homologous recombination occurred were screened, to thereby produce a XQ56 strain (W3110 ΔlacI ΔspeE ΔspeG ΔygjG ΔpuuP ΔpuuA PdapA::Ptrc). The presence of the trc promoter in the strain was confirmed by DNA sequence analysis.

2-2: Preparation of XQ59 Strain

Replacement of the native promoter of the diaminopimelate decarboxylase-encoding lysA gene operon with the trc promoter was performed in the following manner.

The first PCR reaction was performed using the plasmid pECmulox as a template and primers of SEQ ID NOS: 15 and 18.

[SEQ ID NO: 18]:
5'-TAAGTTAACGGCGGCCATTAGCGCTCTCTCGCAATCCGGTAATCC

ATATCATTGACACTATAGAACGCGGCCG-3'

The second PCR reaction was performed using the first PCR product as a template and primers of SEQ ID NOS: 19 and 20.

[SEQ ID NO: 19]:
5'-CTCAGTCAGGCTTCCGGCGGTCATTACCGCATGAAAAATTTCAAT

ATGACGTAAGTTAACGGCGGCCATTA-3'

[SEQ ID NO: 20]:
5'-GATCGGTATCGGTGCTGAACAGTGAATGTGGCATGGTCTGTTTCC

TGTGTGAAATTGTTATCCGCTCACAATTCCACA-3'

The final PCR product was electroporated into the XQ56 strain (W3110 ΔlacI ΔspeE ΔspeG ΔygjG ΔpuuP ΔpuuA PdapA::Ptrc) prepared in Example 2-1, and the resultant cells of the mutant microorganism were cultured on an agar medium containing chloramphenicol while only cells in which double homologous recombination occurred were screened, to thereby produce a XQ59 strain (W3110 ΔlacI ΔspeE ΔspeG ΔygjG ΔpuuP ΔpuuA PdapA::Ptrc PlysA::Ptrc). The presence of the trc promoter in the strain was confirmed by DNA sequence analysis.

2-3: Preparation of XQ60 Strain

Replacement of the native promoter of the dihydrodipicolinate reductase-encoding dapB gene operon with the trc promoter was performed in the following manner.

The first PCR reaction was performed using the plasmid pECmulox as a template and primers of SEQ ID NOS: 15 and 21.

[SEQ ID NO: 21]:
5'-GTCATTCATCGACTCATGCCTTTCACTGATATCCCTCCCTGTTTG

ACACTATAGAACGCGGCCG-3'

The second PCR reaction was performed using the first PCR product as a template and primers of SEQ ID NOS: 22 and 23.

[SEQ ID NO: 22]:
5'-TGGCTCTGGCGTCGTAACCTGTCACATGTTATTGGCATGCAGTCA

TTCATCGACTCATGCC-3'

[SEQ ID NO: 23]:
5'-GGCAACGCGGATGTTTGCATCATGCATGGTCTGTTTCCTGTGTGA

AATTGTTATCCGCTCACAATTCCACA-3'

The third PCR reaction was performed using the second PCR product as a template and primers of SEQ ID NOS: 24 and 25.

[SEQ ID NO: 24]:
5'-GATGTGAAAGGCTTCCAGCAGTGGGTGGCTGAGGTGCTGGCTCTG

GCGTCGTAACCT-3'

[SEQ ID NO: 25]:
5'-TGAATCAACTGGCGGCCCATACGCCCCCCGGCTCCCGCGATGGCA

ACGCGGATGTTTGCAT-3'

The final PCR product was electroporated into the XQ59 strain (W3110 ΔlacI ΔspeE ΔspeG ΔygjG ΔpuuP ΔpuuA PdapA::Ptrc PlysA::Ptrc) prepared in Example 2-2, and the cells of the mutant microorganism were cultured on an agar medium containing chloramphenicol while only cells in which double homologous recombination occurred were screened, to thereby produce a XQ60 strain (W3110 ΔlacI ΔspeE ΔspeG ΔygjG ΔpuuP ΔpuuA PdapA::Ptrc PlysA::Ptrc PdapB::Ptrc). The presence of the trc promoter in the strain was confirmed by DNA sequence analysis.

Example 3

Preparation of Strain Introduced with cadA Gene 3-1: Preparation of p15CadA Plasmid To amplify the cadA gene encoding lysine decarboxylase, PCR was performed using the genomic DNA of *E. coli* W3110 (derived from *E. coli* K-12; λ⁻, F⁻, prototrophic) as a template and primers of SEQ ID NOS: 26 and 27.

[SEQ ID NO: 26]:
5'-CGTCGAATTCATGAACGTTATTGCAATATTG-3'

[SEQ ID NO: 27]:
5'-GCTCGAGCTCTTATTTTTTGCTTTCTTCTTTC-3'

Meanwhile, pTac15K was digested with EcoRI and treated with Mung Bean Nuclease, after which it was digested with SacI to obtain a 4.0-kb DNA fragment. The DNA fragment was ligated with the PCR product (2,168 bp) digested with SacI, and the ligated structure was cloned into *E. coli* TOP 10 (Invitrogen, Carlsbad, Calif., USA) to thereby produce a p15CadA plasmid.

For reference, pTac15K is a plasmid having a p15A origin, a tac promoter and a kanamycin resistance gene and can be constructed in the following manner. First, the plasmid pKK223-3 (Pharmacia Biotech, Uppsala, Sweden) is digested with SphI and treated with Klenow enzyme (New England Biolabs, Ipswich, Mass., USA), and the resulting product is digested with EcoRI to obtain a 0.4-kb DNA fragment. Next, the plasmid pHNC15K is digested with NheI and is treated sequentially with Klenow enzyme and EcoRI to obtain a 3.5-kb DNA fragment. Then, the two DNA fragments are ligated with each other to obtain the plasmid pTac15K. In a manner similar to the preparation of pTac15K, pHNC15K is prepared from the DNA fragment of pACYC177 (New England Biolabs, Ipswich, Mass., USA), pHCE IIB (TaKaRa Korea Biomedical, Seoul, Korea) or pUC4K (Amersham Pharmacia Biotech, Uppsala, Sweden).

p15CadA can constitutively express the cadA gene in lacI-deleted *E. coli* using a strong tac promoter.

3-2: Preparation of WL3110/p15CadA Strain

The p15CadA plasmid prepared in Example 3-1 was electroporated into the WL3110 strain prepared in Example 1-1 to thereby prepare a WL3110/p15CadA strain. The prepared strain was cultured on an agar medium containing kanamycin to thereby select transformed cells.

3-3: Preparation of XQ27/p15CadA Strain

The p15CadA plasmid prepared in Example 3-1 was electroporated into the XQ27 strain prepared in Example 1-5 to thereby prepare a XQ27/p15CadA strain. The prepared strain was cultured on an agar medium containing kanamycin to thereby select transformed cells.

3-4: Preparation of XQ56/p15CadA Strain

The p15CadA plasmid prepared in Example 3-1 was electroporated into the XQ56 strain prepared in Example 2-1 to thereby prepare a XQ56/p15CadA strain. The prepared strain was cultured on an agar medium containing kanamycin to thereby select transformed cells.

3-5: Preparation of XQ59/p15CadA Strain

The p15CadA plasmid prepared in Example 3-1 was electroporated into the XQ59 strain prepared in Example 2-2 to thereby prepare a XQ59/p15CadA strain. The prepared strain was cultured on an agar medium containing kanamycin to thereby select transformed cells.

3-6: Preparation of XQ60/p15CadA Strain

The p15CadA plasmid prepared in Example 3-1 was electroporated into the XQ60 strain prepared in Example 2-3 to thereby prepare a XQ60/p15CadA strain. The prepared strain was cultured on an agar medium containing kanamycin to thereby select transformed cells.

3-7: Preparation of XQ56 ΔaceF/p15CadA Strain

The p15CadA plasmid prepared in Example 3-1 was electroporated into a strain obtained by deleting aceF (dihydrolipoamide acetyltransferase; pyruvate dehydrogenase complex) from the XQ56 strain prepared in Example 2-1, thereby preparing a XQ56 ΔaceF/p15CadA strain. The prepared strain was cultured on an agar medium containing kanamycin to thereby select transformed cells.

Example 4

Production of Cadaverine Using Mutant Microorganisms

Cadaverine degradation and utilization activities together with decarboxylase activity were analyzed through fed-batch fermentation.

The fed-batch fermentation was performed in a 6.6-liter fermentor (Bioflo 3000; New Brunswick Scientific Co., Edison, N.J.) using 2 L of a minimal R2 medium containing 10 g/L glucose and 3 g/L $(NH_4)_2SO_4$. The R/2 medium contains 2 g/L $(NH_4)_2HPO_4$, 6.75 g/L $KH_2PO_4$, 0.85 g/L citric acid, 0.7 g/L $MgSO_4$, $7H_2O$, and 0.5% (v/v) trace metal solution (Qian et al., Biotechnol. and Bioeng, 101(3): 587-601, 2008). The trace metal solution contains, per liter, 5M HCl, 10 g $FeSO_4$, $7H_2O$, 2.25 g $ZnSO_4$, $7H_2O$, 1 g $CuSO_4$, $5H_2O$, 0.5 g $MnSO_4$, $5H_2O$, 0.23 g $Na_2B_4O_7$, $10H_2O$, 2 g $CaCl_2$, $2H_2O$, and 0.1 g $(NH_4)_6Mo_7O_{24}$.

100 μL of each of mutant stains (WL3110/pL15CadA strain, XQ27/p15CadA strain, and XQ56/p15CadA strain)

activated in an LB medium was inoculated into a preparative minimal medium and then cultured at 37° C. at 220 rpm for 24 hours. Then, 1 ml of the culture broth was added to a 350-mL baffled flask containing 50 ml of the same medium, after which it was cultured at 37° C. at 220 rpm for 14 hours. 200 ml of the preculture was used for inoculation into the fermentor, and dissolved oxygen in the fermented broth was maintained with 20% saturated air by automatically controlling the agitation speed. The pH of the fermented broth was maintained at 6.80 by 6M KOH. Also, 100 µL of the mutant strain (XQ56 ΔaceF/p15cadA strain) was inoculated into an LB medium and cultured at 37° C. at 220 rpm for 15 hours. Then, 1 mL of the mutant strain activated in the LB medium was inoculated in a minimal medium and cultured at 37° C. at 220 rpm for 18 hours. The culture was performed in a 350-mL baffled flask using 90 mL of minimal medium+10 mL of 100 g/L glucose. The culture broth was centrifuged to separate cells, and the supernatant was analyzed by HPLC. Cadaverine contained in the supernatant was detected by ophthaldialdehyde (OPA) derivation in a Hewlett Packard 1100 Series system (230 nm) equipped with a C18-reverse phase column. As the mobile phase, buffer A (55% methanol of 0.1 M sodium acetate) and buffer B (methanol) were used.

The analysis was carried out under the following conditions: 1-6 min 100% buffer A equilibration, 6-10 min linear gradient from 0 to 30% buffer B, 10-15 min gradient from 30% to 50% buffer B, 15-19 min gradient from 50% to 100% buffer B, 19-23 min gradient to 100% buffer B, and 23-25 min gradient from 100% to 30% buffer B, 25-28 min from 30% B to 100% A with a flow rate of 0.8 ml/min). Herein, a standard was used for calibration, and the concentrations of cadaverine measured are shown in FIGS. 2 and 4.

Figure 2:
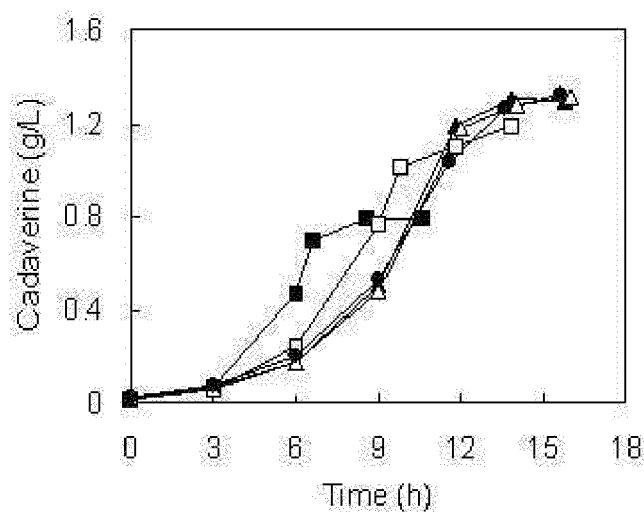
FIG. 2 is a graphic diagram showing the production of cadaverine from WL3110/p15CadA (filled rectangle), XQ27/p15CadA (empty rectangle), XQ56/p15CadA (filled triangle), XQ59/p15CadA (empty triangle) and XQ60/p15CadA (filled circle) strains through fed-batch fermentation using glucose.

As shown in FIG. 2, the production of cadaverine was 0.79 g/l in the WL3110/pL15CadA strain, 1.19 g/l in the XQ27/p15CadA strain wherein the cadaverine degradation and utilization pathways were deleted, and 1.31 g/l in the XQ56/p15CadA strain wherein the dapA encoding dihydrodipicolinate synthase was overexpressed. Also, in the strain wherein the lysA gene encoding diaminopimelate decarboxylase and the dapB gene encoding dihydrodipicolinate reductase were overexpressed, a cadaverine production similar to the above values was shown.

Figure 4:
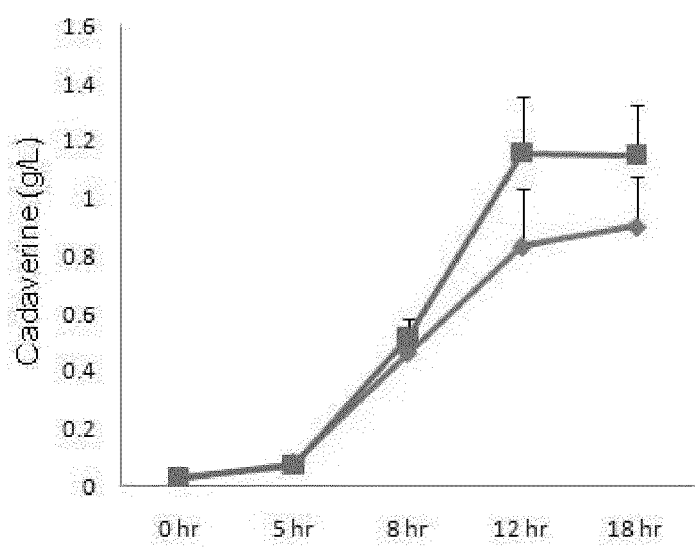
FIG. 4 is a graphic diagram showing the production of cadaverine from XQ56 ΔaceF/p15cadA (filled rectangle) and XQ56/p15CadA (filled lozenge) strains through flask fermentation using glucose.

As shown in FIG. 4, in the XQ56 ΔaceF/p15cadA strain obtained by deleting aceF (dihydrolipoamide acetyltransferase; pyruvate dehydrogenase complex) from the XQ56 strain, the cadaverine productivity was about 1.5 times higher than that of the XQ56/p15cadA strain in flask culture.

Example 5

Production of Cadaverine Through Fed-Batch Culture of XQ56/p15CadA Strain

Fed-batch culture of the XQ56/p15CadA strain was performed in a 6.6-L fermentor of Example 4. As described in Example 4, seed culture was performed in a 350-mL baffled flask containing 50 ml of R/2 medium at 37° C. at 220 rpm for 14 hours. 200 ml of the preculture was used for inoculation into the fermentor, and dissolved oxygen in the fermented broth was maintained with 20% saturated air by automatically controlling the agitation speed.

Figure 3:
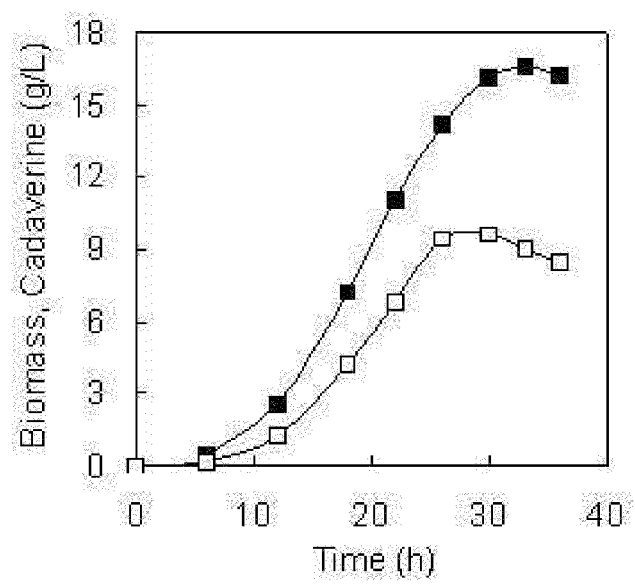
FIG. 3 is a graphic diagram showing cell mass (filled rectangle) and the production of cadaverine (empty rectangle) from a XQ56/p15CadA strain through fed-batch fermentation using glucose.

When the pH of the fermented broth was increased by about 0.01 pH units from a fixed pH of 6.8 as a result of glucose exhaustion, the glucose-containing solution was automatically added in order to increase the glucose concentration to more than 3 g/L. The glucose-containing solution contained 577 g/l glucose, 8 g/L of $MgSO_4$ and 115 g/L of $(NH_4)_2SO_4$. Throughout the entire fermentation period except a short time for which pH was increased due to glucose exhaustion, the pH of the fermented broth was maintained at pH 6.8 by adding 10M KOH. The fermented broth was sampled and centrifuged to separate cells, and the supernatant was analyzed by HPLC in the same manner as described in Example 4. The results are shown in FIG. 3. As shown in FIG. 3, the XQ56/p15CadA strain produced 9.61 g/l of cadaverine at 30 hours after the inoculation, in which the cadaverine productivity was 0.32 g $L^{-1}h^{-1}$.

INDUSTRIAL APPLICABILITY

The present invention is useful for producing a mutant microorganism having a high ability to produce cadaverine and producing a high yield of cadaverine which can be widely used in various industrial applications.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A mutant microorganism having the ability to produce cadaverine wherein the speE gene encoding putrescine/cadaverine aminopropyl transferase, the speG gene encoding spermidine N-acetyltransferase, the ygjG gene encoding putrescine/cadaverine aminotransferase, the puuP gene encoding putrescine importer, and the puuA gene encoding glutamate-putrescine/glutamate-cadaverine ligase, which are involved in the cadaverine degradation or utilization pathway, are inactivated or deleted, wherein the cadA gene encoding lysine decarboxylase is further amplified or introduced into said mutant microorganism, and wherein the native promoter of at least one gene selected from the group consisting of a dapA gene encoding dihydrodipicolinate synthase, a lysA gene encoding diaminopimelate decarboxylase, and a dapB gene encoding dihydrodipicolinate reductase are replaced with a strong promoter.

2. The mutant microorganism of claim 1, wherein a lacI gene encoding a lac operon repressor is further deleted in order to increase the expression of genes encoding enzymes which are involved in cadaverine biosynthesis.

3. The mutant microorganism of claim 1, wherein the cadA gene encoding lysine decarboxylase is introduced in the form of an expression vector containing a strong promoter.

4. The mutant microorganism of claim 3, wherein the strong promoter is selected from the group consisting of a trc promoter, a tac promoter, a T7 promoter, a lac promoter, and a trp promoter.

5. The mutant microorganism of claim 1, wherein the microorganism is selected from the group consisting of *Bacillus* sp., *Corynebacterium* sp., *Escherichia* sp., *Pichia* sp., *Pseudomonas* sp., and *Saccharomyces* sp.

6. A method for preparing a mutant microorganism having the ability to produce cadaverine, the method comprising: inactivating or deleting the speE gene encoding putrescine/cadaverine aminopropyl transferase, the speG gene encoding spermidine N-acetyltransferase, the ygjG gene encoding putrescine/cadaverine aminotransferase, the puuP gene encoding putrescine importer, and the puuA gene encoding glutamate-putrescine/glutamate-cadaverine ligase, which are involved in the cadaverine degradation or utilization pathway from a microorganism having a cadaverine production pathway, wherein the cadA gene encoding lysine decarboxylase is further amplified or introduced into said mutant microorganism, and wherein the native promoter of at least one gene selected from the group consisting of a dapA gene encoding dihydrodipicolinate synthase, a lysA gene encoding diaminopimelate decarboxylase, and a dapB gene encoding dihydrodipicolinate reductase are replaced with a strong promoter.

7. The method of claim 6, wherein a lacI gene encoding a lac operon repressor is further deleted in order to increase the expression of genes encoding enzymes which are involved in cadaverine biosynthesis.

8. The method of claim 6, wherein the cadA gene encoding lysine decarboxylase is introduced in the form of an expression vector containing a strong promoter.

9. The method of claim 8, wherein the strong promoter is selected from the group consisting of a trc promoter, a tac promoter, a T7 promoter, a lac promoter, and a trp promoter.

10. The method of claim 6, wherein the microorganism is selected from the group consisting of *Bacillus* sp., *Corynebacterium* sp., *Escherichia* sp., *Pichia* sp., *Pseudomonas* sp., and *Saccharomyces* sp.

11. A method for producing cadaverine, the method comprising the steps of: culturing the mutant microorganism of claim 1 to produce cadaverine; and recovering cadaverine from the culture.

12. The mutant microorganism of claim 1, wherein the strong promoter is selected from the group consisting of a trc promoter, a tac promoter, a T7 promoter, a lac promoter, and a trp promoter.

* * * * *